United States Patent [19]

Hefti et al.

[11] Patent Number: 4,925,595

[45] Date of Patent: May 15, 1990

[54] LIQUID DETERGENT COMPOSITIONS CONTAINING DISULFONATED FLUORESCENT WHITENING AGENTS: DI-STYRYL-BIPHENYL OR DI-STYRYL-BENZENE DERIVATIVES

[75] Inventors: Heinz Hefti, Reinach, Switzerland; Dieter Reinehr, Kandern, Fed. Rep. of Germany; Kurt Weber, Basle, Switzerland; Claude Eckhardt, Riedisheim, France

[73] Assignee: Ciba-Geigy Corporation, Ardsley, N.Y.

[21] Appl. No.: 212,391

[22] Filed: Jun. 27, 1988

[30] Foreign Application Priority Data

Jul. 3, 1987 [CH] Switzerland ............... 2535/87

[51] Int. Cl.$^5$ .................. C07C 143/29; C11D 3/42
[52] U.S. Cl. .................. 252/301.21; 8/648; 8/918; 252/89.1; 252/550; 252/558; 562/427; 562/83; 562/84; 562/87; 585/25
[58] Field of Search ............ 252/549, 301.21, 558, 252/, 301.21; 260/505 R, 505 C, 507 A; 8/648

[56] References Cited

U.S. PATENT DOCUMENTS

| | | | |
|---|---|---|---|
| 3,980,713 | 9/1976 | Matsuwasa et al. | 585/26 |
| 4,093,645 | 6/1978 | Davidson et al. | 8/648 |
| 4,216,105 | 8/1980 | Davidson et al. | 8/648 |
| 4,298,490 | 11/1981 | Lange et al. | 252/91 |
| 4,533,505 | 8/1985 | Spencer | 585/608 |
| 4,559,169 | 12/1985 | Wevers et al. | 252/543 |

FOREIGN PATENT DOCUMENTS

| | | |
|---|---|---|
| 1923267 | 11/1970 | Fed. Rep. of Germany . |
| 2543998 | 4/1977 | Fed. Rep. of Germany . |
| 2756583 | 6/1979 | Fed. Rep. of Germany . |
| 2808927 | 9/1979 | Fed. Rep. of Germany . |
| 575461 | 5/1976 | Switzerland . |
| 1247934 | 9/1971 | United Kingdom . |

*Primary Examiner*—A. Lionel Clingman
*Attorney, Agent, or Firm*—Edward McC. Roberts

[57] ABSTRACT

Liquid detergent compositions which are stable on storage and contain fluorescent whitening agents from the class of the disulfonated distyrylbiphenyl and distyrylphenyl compounds; they do not produce bleach spots on direct contact with textile fabric. Some of the fluorescent whitening agents used are novel.

11 Claims, No Drawings

LIQUID DETERGENT COMPOSITIONS CONTAINING DISULFONATED FLUORESCENT WHITENING AGENTS: DI-STYRYL-BIPHENYL OR DI-STYRYL-BENZENE DERIVATIVES

The present application relates to liquid detergent compositions which are stable on storage and contain disulfonated distyrylbiphenyl and/or distyrylphenyl compounds as fluorescent whitening agents, as well as anionic, non-ionic or zwitterionic surfactants, and to novel distyrylbiphenyl and distyrylphenyl compounds.

It is commonly known to use fluorescent whitening agents in liquid detergents. They exhaust during the treatment on to the material to be washed and, by virtue of their special light absorption/emission property, result in elimination of the yellowish shades.

However, this effect is also responsible for the appearance of bleach spots if textile fabric comes into direct contact with the liquid detergent, e.g. in a pretreatment. For this reason, European patent application A-167 205 proposes the use of monosulfonated stilbenetriazolyl, triazine or distyrylbiphenyl whitening agents as a solution to this problem.

Surprisingly, it has now been found that the formation of bleach spots, with no change in the excellent whitening effect and detergent stability, can be prevented by incorporating certain disulfonated distyrylbiphenyl and/or distyrylphenyl compounds as fluorescent whitening agents into liquid detergent compositions.

The present application thus relates to liquid detergent compositions containing fluorescent whitening agents, wherein the fluorescent whitening agents present in an amount of 0.01 to 2% consist of a disulfonic acid whitening agent or a mixture of disulfonic acid whitening agents of the formula (I)

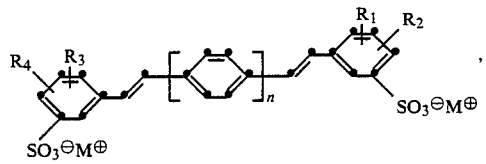

wherein
R$_1$, R$_2$, R$_3$, R$_4$=H, Hal and/or C$_1$-C$_4$ alkyl, or R$_1$, R$_2$ and R$_3$ and R$_4$ are forming each a cyclohexane residue
n=1 or 2
M$^\oplus$=a salt-forming cation.

It is preferred to use disulfonic acid whitening agents of the formula (II)

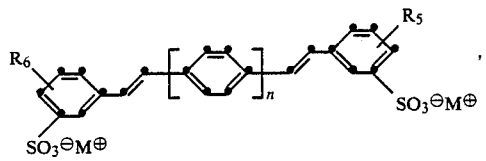

wherein
R$_5$, R$_6$=H, Cl, F, CH$_3$
M$^\oplus$=H, Na, K, Li, NH$_4$, NH(CH$_2$—CH$_2$OH)$_3$

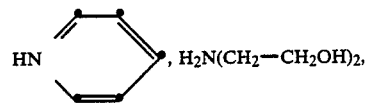, H$_2$N(CH$_2$—CH$_2$OH)$_2$,

H$_2$N(CH$_2$—CH$_2$OH)$_2$,
H$_3$N—CH$_2$CH$_2$OH, H$_2$N(CH$_3$)$_2$, H$_3$N—CH$_3$
n=1 or 2.
However, disulfonic acid whitening agents of the formula (III) or (IV)

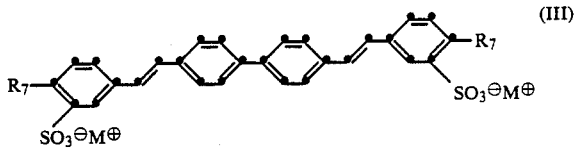

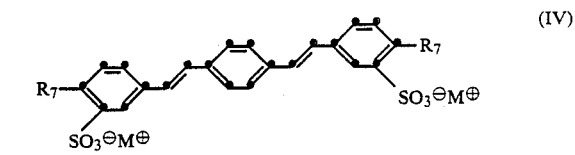

are especially preferred, as are mixtures of 1 to 10 parts, preferably 1 to 5 parts, of the compounds of the formula III with 10 to 1 part, preferably 5 to 1 part, of the compounds of the formula IV, wherein R$_7$=H, Cl, F or CH$_3$ and M$^+$ is as defined above.

The term liquid detergent compositions will be understood as meaning the known and commercially available detergent compositions described, for example, in European patent application A-167 205 or U.S. Pat. No. 4 507 219.

In particular, the liquid detergents contain 1 to 60% of anionic, non-ionic, zwitterionic and, in some cases, cationic surfactants and 25 to 65% preferably 40 to 55%, of water. Specifically, the detergent composition contains, in addition to the fluorescent whitening agent, 3 to 50%, preferably 15 to 25%, of anionic surfactants, 2 to 30%, preferably 4 to 15%, of non-ionic surfactants, 3 to 30%, preferably 5 to 20%, of ethoxylated or non-ethoxylated (C$_{10}$-C$_{22}$) fatty acids, especially saturated (C$_{10}$-C$_{24}$) fatty acids such as capric, lauric and myristic acids and coconut and palm kernel fatty acids and mixtures thereof, 1 to 25%, preferably 1 to 10%, of builders and, if appropriate, 1 to 10%, preferably 1 to 5%, of zwitterionic surfactants, 0.5 to 3%, preferably 0.7 to 2%, of quaternary ammonium, amine or amine oxide surfactants and 1 to 10% of conventional detergent additives such as enzymes, enzyme stabilizers, antioxidants, preservatives and disinfectants, fragrances and dyes, complexing agents and/or sequestering agents and solvents.

Useful surfactants are described e.g. in U.S. Pat. Nos. 4 285 841, 3 929 678 and 4 284 532 and British patent 2 041 986. The surfactants designated as preferred surfactants in European patent application A-167 205 are used in particular. However, anionic surfactants which are preferably used are ethoxylated or non-ethoxylated C$_{10}$-C$_{18}$alkylsulfates, e.g. in the form of the triethanolamine salts, C$_{10}$-C$_{15}$alkylbenzenesulfonates or mixtures thereof, and non-ionic surfactants which are preferably used are condensation products of one mol of (C$_{10}$-C$_{15}$) fatty alcohol with 3 to 8 mol of ethylene oxide.

Suitable builders are the preferably polycarboxylated compounds mentioned in U.S. Pat. Nos. 4 321 165 and 4 284 532, for example citric acid or citrates.

The present application further relates to the compounds of the formulae

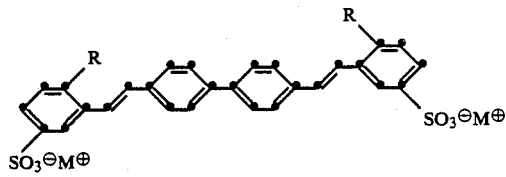

(V)

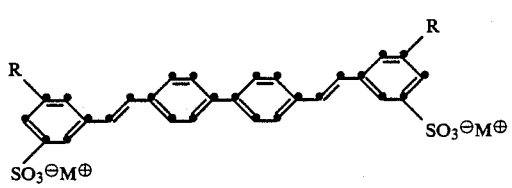

(VI)

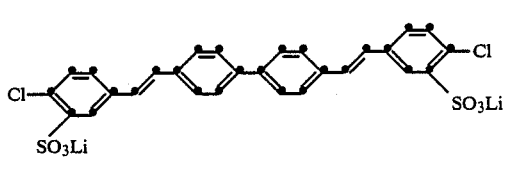

(VII)

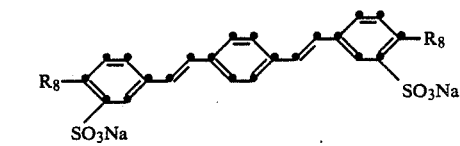

(VIII)

where $R_8$ = H or F wherein $M^\oplus$=H, Na, K, Li, NH$_4$, HN(CH$_2$—CH$_2$OH)$_3$, H$_2$N(CH$_2$—CH$_2$OH)$_2$, H$_3$N—CH$_2$—CH$_2$OH, H$_2$N(CH$_3$)$_2$, H$_3$N—CH$_3$ or

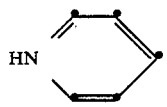

R=C$_1$-C$_4$alkyl.

The compounds of the formulae (V), (VI), (VII) and (VIII) are novel and can be obtained by reacting the compound of the formula (IX) or (X)

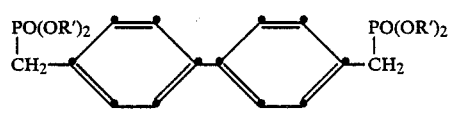

(IX)

(X)

where R′=C$_1$-C$_4$alkyl
in an aprotic solvent, e.g. DMSO, DMF, acetonitrile, HMPT, benzene or chlorobenzene, with compounds of the formula (XI), (XII) or (XIII)

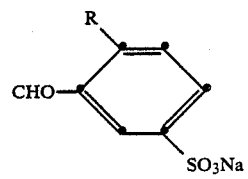

(XI)

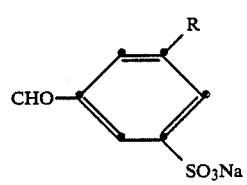

(XII)

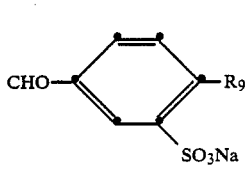

(XIII)

where $R_9$=H, Cl, F
in the presence of bases, e.g. alkali metal or alkaline earth metal hydroxides or alcoholates.

The novel compounds possess excellent whitening properties, are stable in detergents and soluble in water, have good absorption and migration properties and good whitening effects on cellulosic material and do not form bleach spots. They are particularly suitable for use in liquid detergents.

The following Examples will serve to illustrate the invention. Parts and percentages are by weight. The spotting test is carried out in the following manner:

Spotting Test (a) Whitening agent/detergent formulation:

0.1% (100% of active substance) of fluorescent whitening agent or mixture of fluorescent whitening agents is dissolved in a liquid detergent. If a fluorescent whitening agent is insoluble in the finished formulation of a liquid detergent composition, the fluorescent whitening agent is first dissolved in the water/solvent or surfactant/solvent mixture of the detergent composition in question and the remaining detergent additives are then incorporated.

(b) Bleached cotton fabric is padded with the whitening agent/detergent formulation. The pick-up is 70%. The fabric is then dried in air for 15 minutes.

(c) 1 part of fabric (A) padded according to (b) and 9 parts of bleached cotton fabric (B) are washed together for 15 minutes at 30° C. with no other additives (liquor ratio 1:20). The fabric are then rinsed with water and dried at 70° C.

(d) After washing, the difference in the degree of whiteness (measured by the Ciba-Geigy White Scale using a Zeiss RFC3 photometer) between the padded test fabric (A) and the fabric (B) is determined. A fluorescent whitening agent shows a slight tendency to form bleach spots when the difference between the degree of whiteness of the padded fabric (A) and the fabric (B) is small.

EXAMPLE 1

The spotting test is carried out with fluorescent whitening agents of the formulae

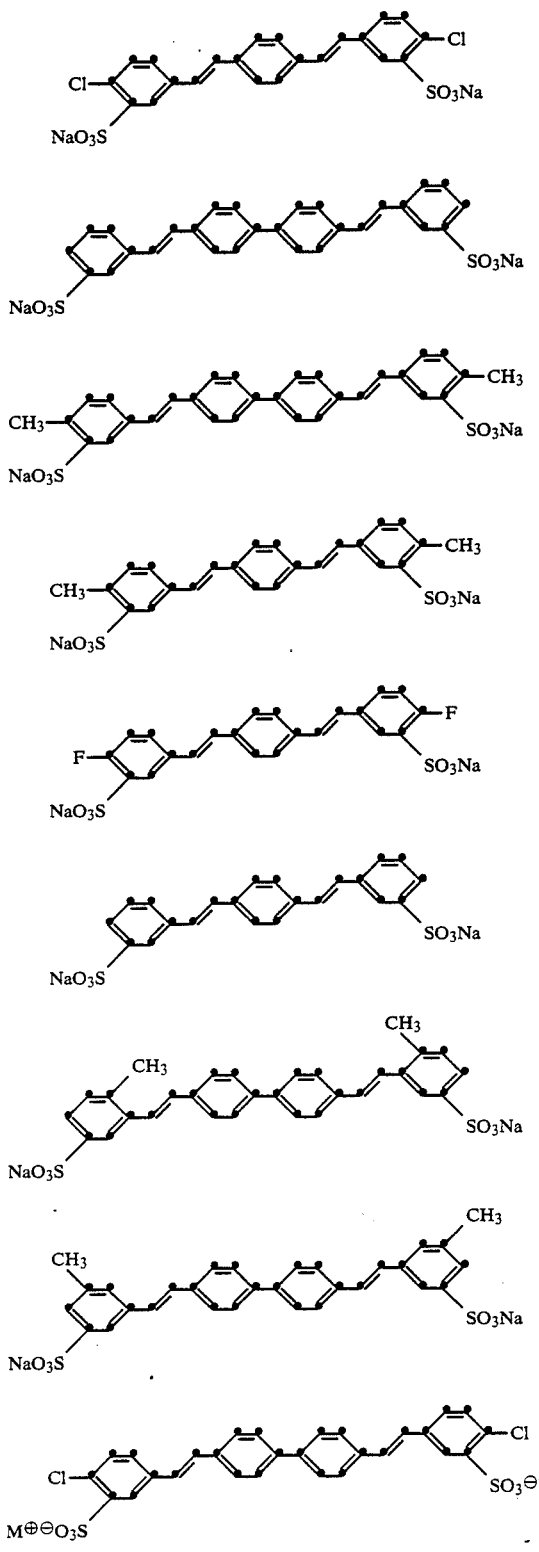

| | M⊕ | |
|---|---|---|
| H | | (9) |
| Li | | (10) |
| Na | | (11) |
| K | | (12) |
| NH4 | | (13) |
| | HN(CH2—CH2OH)3 | (15) |
| | H2N(CH2—CH2OH)2 | (16) |
| | H3N CH2—CH2OH | (17) |
| | H2N (CH3)2 | (18) |
| | H3N—CH3 | (19) |

| | M⊕ | |
|---|---|---|
| |  | (14) | and with the following mixtures

| (20) | 4 parts of compound (1) with 1 part of compound (3) |
| (21) | 1 part of compound (1) with 1 part of compound (3) | and a liquid detergent containing
  15% of $C_{11}$-$C_{13}$alkylbenzenesulfonate
  14% of polyethoxylated $C_{14}$-$C_{15}$ fatty alcohol (ethylene oxide 7)
  10% of soap flakes
  9% of ethanol
  4% of sodium citrate
  5% of triethanolamine
  43% of water.
All the compounds are stable for several months in the detergent composition, have a good whitening effect and induce no, or only insignificant, spotting.

EXAMPLE 2

The spotting test is carried out with compounds of the formulae (1)–(19) and with the mixtures (20) or (21) and a liquid detergent composition containing
  7.5% of $C_{13}$alkylbenzenesulfonate
  12% of $C_{14}$-$C_{15}$alkylpolyethoxysulfonate (ethylene oxide 2.25)
  15% of $C_{11}$-$C_{13}$ fatty acid, potassium salt
  10% of polyethoxylated $C_{12}$-$C_{14}$ fatty alcohol (ethylene oxide 8)
  5.5% of sodium citrate
  12% of a 1:1 mixture of isopropyl alcohol and spirit
  0.7% of $C_{12}$alkyltrimethylammonium chloride
  37.3% of water.
All the compounds are stable for several months in the detergent, have a good whitening effect and induce no, or only insignificant, spotting.

EXAMPLE 3

The spotting test is carried out with compounds of the formulae (1)–(19) and with the mixtures (20) or (21) and a liquid detergent containing
  11.5% of $C_{11}$-$C_{13}$alkylbenzenesulfonate
  3.8% of triethanolamine laurylsulfate
  15.5% of potassium soap
  15% of polyethoxylated $C_{14}$-$C_{15}$ fatty alcohol (ethylene oxide 7)
  5% of triethanolamine
  10% of ethanol
  39.2% of water.
All the compounds are stable for several months in the detergent, have good whitening properties and induce no, or only insignificant, spotting.

EXAMPLE 4

30 g of the compound of formula (9) are added to 600 ml of water at 90° C., with stirring. After the addition of 4.2 g of lithium hydroxide monohydrate, the mixture is stirred for 2 hours at 95° C. and left to cool to room temperature. The precipitated product is isolated by suction filtration and the moist filter cake is recrystallized from a mixture of 200 ml of dimethylformamide, 400 ml of ethanol and 400 ml of water with the aid of active charcoal. After drying under vacuum, the yield of compound (10) is 19 g.

EXAMPLE 5

(a) 10.2 g of sodium methylate (content: 96%) are added to 100 ml of dimethylformamide, with stirring. A solution of 31.7 g of 4,4'-bis(dimethylphosphonomethyl)biphenyl (content: 94.3%) and 33.3 g of sodium 2-methylbenzaldehyde-5-sulfonate in 600 ml of dimethylformamide is added dropwise at 40°–45° C. over a period of 3 hours. After the addition of 100 ml of water, the mixture is neutralized with 5 ml of concentrated hydrochloric acid and evaporated to dryness and the residue is recrystallized from a mixture of 200 ml of water and 600 ml of ethanol. Yield: 17.7 g of the compound of formula (7).

(b) Sodium 2-methylbenzaldehyde-5-sulfonate can be obtained in the following manner:

120 g of 2-methylbenzaldehyde are added dropwise to 300 ml of 66% oleum over a period of 1½ hours, with stirring, whereupon the temperature rises to 49° C. The reaction mixture is cooled to room temperature, poured onto 1.5 kg of ice and neutralized with 1450 g of barium carbonate. The barium sulfate is filtered off with suction and washed with water and the filtrate is concentrated to 800 ml on a rotary evaporator. After cooling to 0°–5° C., the barium salt which has crystallized out is isolated by suction filtration and dissolved in 1000 ml of hot water, and 22.5 g of sulfuric acid (content: 95.7%) are added dropwise. The precipitate of barium sulfate is filtered off hot with suction and the filtrate is neutralized with 2N sodium hydroxide solution and evaporated to dryness. Yield: 91 g of sodium 2-methylbenzaldehyde-5-sulfonate.

(c) Following a procedure analogous to that described in section (a) of this Example, the compound of the formula (8) can be obtained by using sodium 2-methylbenzaldehyde-5-sulfonate.

Sodium 3-methylbenzaldehyde-5-sulfonate can be obtained, as described in Example 3(b), by the sulfonation of 3-methylbenzaldehyde with 66% oleum and isolation via the barium salt.

EXAMPLE 6

(a) 6.8 g of sodium 4-fluorobenzaldehyde-3-sulfonate and 5.7 g of tetraethyl p-xylylene-bis-phosphonate are added to 50 ml of DMF, with stirring. 5.9 g of a 30% sodium methylate solution are added dropwise over a period of 30 minutes (temp.: 40°–45° C.). The mixture is stirred for a further 6 hours at 40°–45° C. and neutralized with glacial acetic acid and the product is isolated by suction filtration and washed with methanol. Yield: 4.8 g of the compound of formula (5).

(b) Sodium 4-fluorobenzaldehyde-3-sulfonate can be obtained as described in Example 5(b).

EXAMPLE 7

Following the same procedure, compound (6) is obtained in similar yield by using sodium benzaldehyde-3-sulfonate instead of sodium 4-fluorobenzaldehyde-3-sulfonate.

What is claimed is:

1. A liquid non-spotting detergent composition containing a whitening agent, wherein the fluorescent whitening agent present in an amount of 0.01 to 2% consists of a disulfonic acid whitening agent or a mixture of disulfonic acid whitening agents of the formula (I)

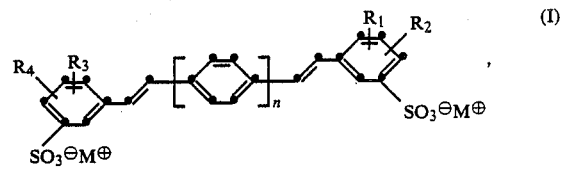

wherein $R_1$, $R_2$, $R_3$ and $R_4$ independently from each other is H, Hal and/or $C_1$–$C_4$alkyl, n is 1 or 2, $M^\oplus$ is hydrogen or an alkali metal ion, except those compounds in which $R_1$ or $R_2$ and $R_3$ or $R_4$ are chlorine para to the stilbene residue and n is 2.

2. A liquid detergent composition according to claim 1, which contains disulfonic acid whitening agents or a mixture of disulfonic acid whitening agents of the formula (II)

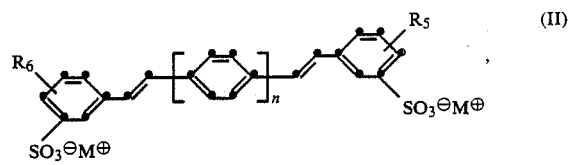

wherein $R_5$, $R_6$ is H, Cl, F, $CH_3$, $M^\oplus$ is H, Na, K or Li, and n is 1 or 2.

3. A liquid detergent composition according to claim 2, which contains disulfonic acid whitening agents of the formula (III)

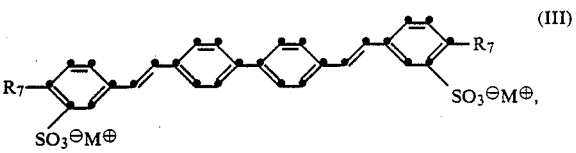

wherein $R_7$ is H, F or $CH_3$ and $M^\oplus$ is as defined in claim 2.

4. A liquid detergent composition according to claim 2, which contains disulfonic acid whitening agents of the formula (IV)

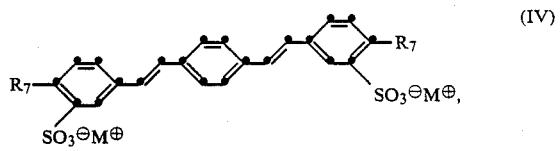

wherein $R_7$=H, Cl, F or $CH_3$ and $M^\oplus$ is as defined in claim 2.

5. A liquid detergent composition according to claim 2, which contains a mixture of disulfonic acid whitening agents of the formula (III)

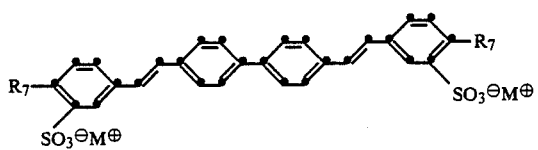

(III)

with disulfonic acid whitening agents of the formula (IV)

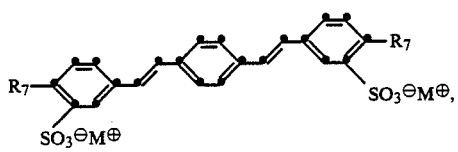

(IV)

wherein $R_7$ is H, Cl, F or $CH_3$ and $M^\oplus$ is as defined in claim 2.

6. A liquid detergent composition according to claim 1, which contains 25% to 65% of water, 3% to 50% of anionic surfactants, 2% to 30% of non-ionic surfactants, 3% to 30% of ($C_{10}$–$C_{22}$) fatty acids, 1 to 10% of builders and, if appropriate, other detergent additives.

7. A compound of the formula (V)

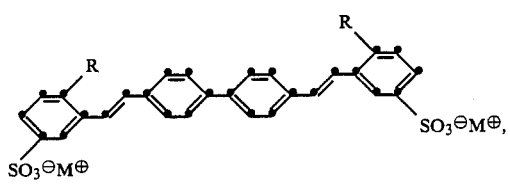

(V)

wherein
$M^\oplus$ is H, Na, K or Li, and
$R = C_1$–$C_4$alkyl.

8. A compound of the formula (VI)

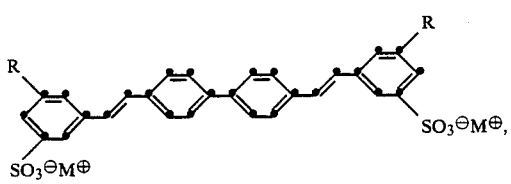

(VI)

wherein
$M^\oplus$ is H, Na, K, Li, and
$R = C_1$–$C_4$alkyl.

9. A compound of the formula (VIII)

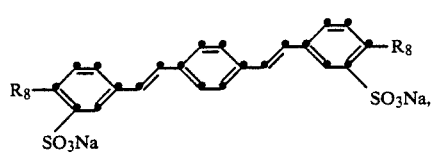

(VIII)

wherein $R_8 = F$.

10. A process for the preparation of a compound of the formula (V)

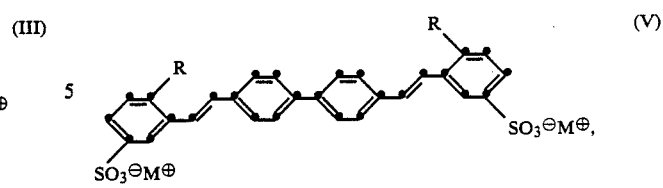

(V)

wherein
$M^\oplus$ is H, Na, K or Li, and
R is $C_1$–$C_4$alkyl,
or a compound of the formula (VI)

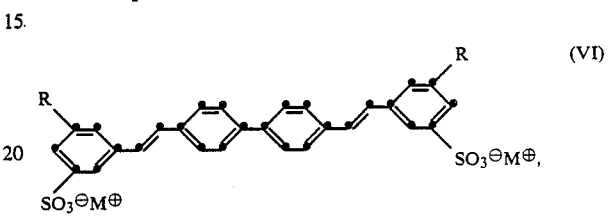

(VI)

wherein
$M^\oplus$ is H, Na, K or Li, and
R is $C_1$–$C_4$alkyl,
which comprises reacting the compound of the formula (IX) or (X)

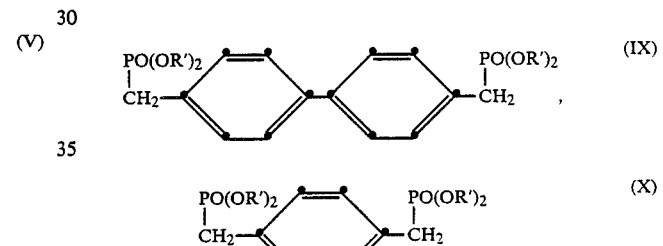

where $R' = C_1$–$C_4$alkyl in an aprotic solvent, with a compound of the formula (XI) or (XII)

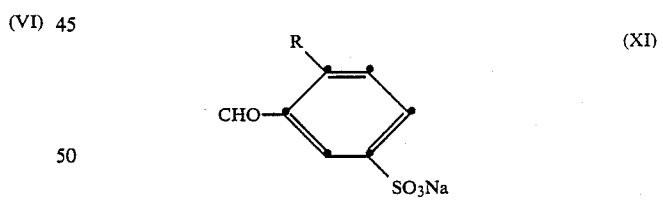

in the presence of a base, and, if desired, subsequently converting the reaction product into the free acid or a salt.

11. A method of whitening cellulosic texture fabrics comprising the step of applying thereto a detergent composition comprising as whitening agent a compound of formula

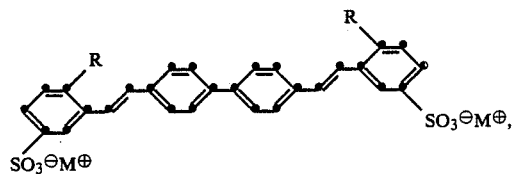 (V)
wherein
 $M^\oplus$ is H, Na, K or Li, and
 R is $C_1$–$C_4$alkyl,
or a compound of the formula (VI)
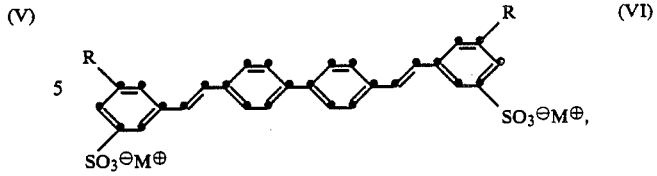 (VI)
wherein
 $M^\oplus$ is H, Na, K or Li, and
 R is $C_1$–$C_4$alkyl.
* * * * *